(12) United States Patent
Choi et al.

(10) Patent No.: US 7,241,441 B2
(45) Date of Patent: Jul. 10, 2007

(54) **MICROORGANISM *PEDIOCOCCUS PENTOSACEUS* EROM101, HAVING IMMUNE ENHANCEMENT, ANTICANCER AND ANTIMICROBIAL ACTIVITIES**

(75) Inventors: Chang Won Choi, Gyeonggi-do (KR); Mi Hyoun Park, Seoul (KR); Sang Ho Hwang, Seoul (KR); Suk Gyu Woo, Gyeonggi-do (KR); Mi Kyung Song, Seoul (KR); Jong Jun Im, Seoul (KR); Sung Gil Hong, Seoul (KR); Joong Hark Kim, Seoul (KR); Jung Soon Jang, Seoul (KR); Hwa Young Kim, Seoul (KR)

(73) Assignee: Eromlife Co., Ltd., Seoul (KR)

( * ) Notice: Subject to any disclaimer, the term of this patent is extended or adjusted under 35 U.S.C. 154(b) by 0 days.

(21) Appl. No.: 11/450,452

(22) Filed: Jun. 12, 2006

(65) Prior Publication Data

US 2006/0228379 A1 Oct. 12, 2006

Related U.S. Application Data

(63) Continuation of application No. 10/732,340, filed on Dec. 11, 2003, now abandoned.

(51) Int. Cl.
*A01N 63/00* (2006.01)
*A01N 65/00* (2006.01)
*C12N 1/20* (2006.01)
*A61K 39/02* (2006.01)

(52) U.S. Cl. ............... 424/93.45; 424/93.4; 424/93.1; 424/184.1; 424/234.1; 424/277.1; 435/252.9; 435/243; 435/822

(58) Field of Classification Search ............ 424/93.4, 424/184.1, 234.1, 277.1, 93.45, 93.1; 435/243, 435/822, 252.9; 530/350
See application file for complete search history.

(56) References Cited

U.S. PATENT DOCUMENTS

2001/0014322 A1 8/2001 Chen et al.
2004/0028665 A1 2/2004 Garner et al.

OTHER PUBLICATIONS

Perdigon et al., "The Oral Administration of Lactic Acid Bacteria Increase the Mucosal Intestinal Immunity in Response to Enteropathogens," *Journal of Food Protection*, 1990, vol. 53, No. 5, pp. 404-410, International Association of Milk, Food and Environmental Santiarians, Argentina.
Sato et al., "Enhancement of Host Resistance against *Listeria* Infection by *Lactobacillus casei*: Activation of LIver Macrophages and Peritoneal Macrophages by *Lactobacillus casei*," *Microbiol. Immunol.*, 1988, vol. 32, No. 7, pp. 689-698, Japanese Society for Bacteriology, Tokyo, Japan.
Barros et al., "Phenotypic and Genotypic Characterization of *Pediococcus* Strains Isolated from Human Clinical Sources," *Journal of Clinical Microbiology*, 2001, vol. 39, No. 4, pp. 1241-1246, American Society for Microbiology, Washington, D.C.

*Primary Examiner*—Robert A. Zeman
*Assistant Examiner*—Lakia J. Tongue
(74) *Attorney, Agent, or Firm*—Buchanan Ingersoll & Rooney PC (57) ABSTRACT

The present invention relates to a novel *Pediococcus* genus microorganism and more particularly, *Pediococcus pentosaceus* EROM101 (KCCM-10517) originated from human intestines having immune enhancement, anticancer and antiviral activities and a use thereof. Due to its excellent immune enhancement, anticancer and antimicrobial activities by activating macrophages/spleen cells and inducing gut immunity, the *Pediococcus pentosaceus* EROM101 of the present invention can be effectively used for the production of various products such as immune enhancement agent, anticancer agent, antimicrobial agent, food additive, intestinal function-controlling agent, live bacterial agent, feed additive and other fermented products.

1 Claim, 11 Drawing Sheets

MICROORGANISM *PEDIOCOCCUS PENTOSACEUS* EROM101, HAVING IMMUNE ENHANCEMENT, ANTICANCER AND ANTIMICROBIAL ACTIVITIES

FIELD OF THE INVENTION

The present invention relates to a novel *Pediococcus* genus microorganism and more particularly, *Pediococcus pentosaceus* EROM101 (KCCM-10517) originated from human intestines having immune enhancement, anticancer and antimicrobial activities and a use thereof.

BACKGROUND OF THE INVENTION

Lactic acid bacteria are the bacteria metabolizing carbohydrate and producing lactic acid thereby. These bacteria belong to facultative anaerobes or obligatory anaerobes which proliferate well under anaerobic conditions. Lactic acid bacteria are divided into 5 genuses, which are *Streptococcus*, *Lactobacillus*, *Leuconostoc*, *Bifidobacteria* and *Pediococcus*. A *Streptococcus* genus microorganism is a homofermentive bacterium that generates lactic acid by fermenting milk to suppress putrefying bacteria or pathogenic bacteria. A *Lactobacillus* genus microorganism is a bacilliform, and a homo- or heterofermentive bacterium, which is widely seen in the fermentation of dairy products or vegetables. A *Leuconostoc* genus microorganism, a *diplococcus*, is a heterofermentive bacterium and mostly involved in fermenting vegetables. A *Bifidobacteria* genus microorganism is an obligatory anaerobe which generates L(+) lactic acid useful for children's health, but cannot survive under aerobic conditions. Lastly, a *Pediococcus* genus microorganism is a homofermentive bacterium having the form of *tetracoccus*, which is mostly found in Kimchi or brined foods and involved in the fermentation of meats including sausages. Among them, *Bifidobacteria* are the major obligatory anaerobic lactic acid bacteria found in human intestines, and they are counted 100–1000 times as many as facultative anaerobic lactic acid bacteria such as *Lactobacillus* and *Streptococcus* in human intestine.

Lactic acid bacteria control pH of intestines to keep them acidic condition, so that they inhibit the proliferation of harmful bacteria like *E. coli* or *Clostridium* sp. And they moderate diarrhea and constipation, and play an important role in vitamin synthesis, anticancer activity, lowering serum cholesterol and the like. Particularly, lactic acid bacteria have a specific protein that can be adhered tightly to mucosa and epithelial cells of intestines, to have an intestinal function-controlling effect inhibiting the growth of harmful bacteria. In addition, lactic acid bacteria stimulate the proliferation of macrophages, resulting in the enhancement of the capability of macrophage to recognize and sterilize harmful bacteria invaded in intestines. They, further, stimulate the secretion of immune-related substances, resulting in the enhancement of the immunity (Gabriela perdigon et al., *J. of food Protection* 53:404–410, 1990; Katsumasa sato et al., *Microbiol. Immunol.*, 32(7):689–698, 1988). Especially, *Lactobacillus* genus microorganism produces acidophillin to inhibit the growth of harmful bacteria such as dysentery bacillus (*Shigella*), *salmonella* and *staphylococcus*, and the proliferation of causal bacteria of diarrhea, resulting in the normalization of intestinal flora and the cease of diarrhea. In addition, *Pediococcus pentosaceus* has been confirmed to have an excellent ability to inhibit the growth of harmful bacteria such as *Helicobacter pylori*, *Listeria* sp. and the like by secreting a strain specific antibacterial peptide.

Recently, studies have actively been progressing about separating lactic acid bacteria and developing a live bacterial medicine, food additive and intestinal function-controlling agent using the same, in order to keep minor lactic acid bacteria inhabiting human intestines longer. Korean patent No.264295 discloses "Novel *Bifidobacterium longum* MK-G7 bifidus strain having a physiological activity suitable to Koreans and a use thereof", and Korean patent No.158049 discloses "*Bifidobacterium longum* HS90 producing mucopolysaccharide having an excellent humidness". Also, Korean patent No.2000-316517 discloses "Novel *Lactobacillus acidophilus* YD9904 strain having an excellent acid producing ability and acid resistance, and a product containing the same", and the Korean patent No.2001-70689 discloses "*Lactobacillus acidophilus* 30SC having a great acid resistance and bile-tolerant activity as well as an antibacterial activity of inhibiting the growth of pathogenic bacteria and putrefying bacteria". Korean patent No.2001-11797 discloses "Novel acid-tolerant *Lactobacillus luteri* probio-16 having an antimicrobial activity against rotavirus and harmful microorganism, and live bacterial activator containing the same". That is, almost all the studies about lactic acid bacteria have been focused on *Lactobacillus* genus microorganisms and *Bifidobacterium* genus microorganisms having an acid-tolerant and/or an anti-microbial activity.

SUMMARY OF THE INVENTION

Accordingly, it is an object of the invention to provide novel lactic acid bacteria having an excellent physiological activity and inhabiting human intestines stably and a use thereof. In the course of conducting continuous studies to develop novel lactic acid bacteria having an immune enhancement activity, the present inventors separated a novel *Pediococcus* genus microorganism from human excrements and identified that the said microorganism has immune enhancement, anticancer and antimicrobial activities, and thus they have completed the present invention. *Pediococcus pentosaceus* EROM101, or mutant or variant thereof of the present invention showed excellent immune enhancement, anticancer and antimicrobial activities by stimulating the activities of macrophages/spleen cells and gut immunity, so that they can be used for the production of various products such as immune enhancement agent, anticancer agent, antimicrobial agent, food additive, intestinal function-controlling agent, live bacterial agent, feed additive and other fermented products.

BRIEF DESCRIPTION OF THE DRAWINGS

A: Comparison with a test strain

B: Proliferation rate according to cell concentration

A: Comparison of macrophage activity between live bacteria EROM101 (ER) and cell lysate thereof (EL)

B: Comparison of macrophage activity between EROM101 cell lysate (EL) and *Lactobacillus acidophilus* (test strain) cell lysate (LL)

EL: Group treated with EROM101 cell lysate

LL: Group treated with *Lactobacillus acidophilus* cell lysate

Con: Control group

ER: Group administered orally with live bacteria of EROM101

EL: Group administered orally with cell lysate of EROM101

LR: Group administered orally with live bacteria of *Lactobacillus acidophilus*

LL: Group administered orally with cell lysate of *lactobacillus acidophilus*

ER: Group administered orally with live bacteria of EROM101

EL: Group administered orally with cell lysate of EROM101

LR: Group administered orally with live bacteria of *Lactobacillus acidophilus*

LL: Group administered orally with cell lysate of *lactobacillus acidophilus*

A: Positive control (LPS-treated group)

B: Positive control (ConA-treated group)

ER: Group administered orally with live bacteria of EROM101

EL: Group administered orally with cell lysate of EROM101

LR: Group administered orally with live bacteria of *Lactobacillus acidophilus*

LL: Group administered orally with cell lysate of *lactobacillus acidophilus*

EL: Group administered orally with cell lysate of EROM101

LL: Group administered orally with cell lysate of *Lactobacillus acidophilus*

EC-group: Cell lysate of EROM101 of the present invention was injected into the abdominal cavity after the injection of cancer cells LC-group: Cell lysate of *Lactobacillus acidophilus* was injected into the abdominal cavity after the injection of cancer cells TC-group: Saline was administered after the injection of cancer cells

DETAILED DESCRIPTION OF THE INVENTION

The present invention provides a *Pediococcus pentosaceus* EROM101 having immune enhancement, anticancer and antimicrobial activities, which was originated from human intestines.

It is known in the art to obtain mutants of microorganisms without altering the characteristic thereof. For instance, mutants may be obtained by treatment with physical or chemical mutagens such as UV light, X-rays, gamma-rays and n-methyl-N'-nitro-N-nitrosoguanidine. It is also known in the art to obtain natural variants by e.g. screening cultures of the parent strain. Therefore, the invention also pertains to the mutants or variants of *Pediococcus pentosaceus* EROM101 which retain the characteristics of the parent strains e.g. the immune enhancement, anticancer and antimicrobial activities.

The present invention also provides a composition containing the above *Pediococcus pentosaceus* EROM101, or mutant or variant thereof for immune enhancement agent, anticancer agent, antimicrobial agent, intestinal function-controlling agent, live bacterial agent, feed additive and food additive.

The present invention further provides fermented products containing the above *Pediococcus pentosaceus* EROM101, or mutant or variant thereof.

The present invention also provides a method for culturing the above *Pediococcus pentosaceus* EROM101, or mutant or variant thereof.

The present invention also provides a method for enhancing immunity in a subject, comprising administering an effective amount of a biologically pure culture of the above *Pediococcus pentosaceus* EROM101, or mutant or variant thereof to a subject.

The present invention further provides a method for treating cancer in a subject, comprising administering an effective amount of a biologically pure culture of the above *Pediococcus pentosaceus* EROM101, or mutant or variant thereof to a subject.

The present invention also provides a method for treating microbial infection in a subject, comprising administering an effective amount of a biologically pure culture of the above *Pediococcus pentosaceus* EROM101, or mutant or variant thereof to a subject.

The present invention further provides a method for controlling the microbial growth, comprising contacting the above *Pediococcus pentosaceus* EROM101, or mutant or variant thereof with other microorganisms.

The present invention will be described in detail.

The present invention provides a novel *Pediococcus* genus microorganism having excellent immune enhancement, anticancer and antimicrobial activities. In order for lactic acid bacteria to work effectively in human, they ought to inhabit human intestines stably and have anti-bile activity and acid resistance. Thus, in order to produce products containing lactic acid bacteria for human, the lactic acid bacteria are required to be originated from human. So, the present inventors have separated a *Pediococcus* genus microorganism from human excrements, which is originated from human intestines and has an excellent immune enhancement activity. First, a number of lactic acid bacteria were selectively separated from human excrements by using LBS agar medium, a lactic acid bacteria selection medium. Then, biomass obtained from the culture of each strain was cultured along with macrophages. A microorganism that showed the highest macrophage proliferation rate was separated and identified. As macrophages for this invention, those separated from the abdominal cavity of a mammal are preferable, and particularly in this invention, macrophages separated from the abdominal cavity of a mouse were used. The separated microorganisms can be identified by using the classification standard of the Bergey's manual and analysis program with microorganism identification kit, based on the morphological, cultural and physiological characteristics of those microorganisms. Also, the identification can be accomplished by investigating the physiological phenomena such as Gram staining, oxygen requirement, nutritional requirement, magnetic susceptibility, metabolite, enzyme reaction, antibiotics resistance and the like by the molecular genetic analysis method using DNA base sequence and 16S RNA structure, by the chemical analysis method using the contents of a cell wall, quinone type of electron transport system and the MIDI composition, and by the immunological method. Particularly, in this invention, the microorganism of the invention was identified by analyzing the result obtained by using API 50 CHL kit (BioMereux Co., France), a microorganism identification kit, with API LAB plus database V 5.0. As a result, the microorganism separated by the present inventors was confirmed to have 99.9% identity with *Pediococcus pentosaceus*. Accordingly, the present inventors named the microorganism '*Pediococcus pentosaceus* EROM101', and deposited it at the Korean Culture Center of Microorganisms, 361–221, Yurim B/D, Hongje-1-dong, Sodaemun gu, Seoul 120-091, Republic of Korea, on Jul. 19, 2002. The original deposit was requested on Oct. 10, 2003 to be converted under the Budapest Treaty and was assigned Accession No. KCCM-10517.

*Pediococcus pentosaceus* EROM101 of the present invention has following physiological characteristics;

First, the microorganism stimulates the macrophage proliferation depending on cell concentration, and enhances cellular immunity by macrophages, humoral immunity by spleen cells and gut immunity.

Second, the microorganism significantly inhibits the cancer cell proliferation.

Third, the microorganism shows a wide antimicrobial spectrum against various harmful microorganisms.

Thus, *Pediococcus pentosaceus* EROM101 of the present invention, or mutant or variant thereof can be effectively used as a use for the enhancement of human or animal health, i.e., a composition for immune enhancement agent, anticancer agent, antimicrobial agent, intestinal function-controlling agent, live bacterial agent or feed additive. The composition can include crushed cell wall fraction, live bacteria, killed bacteria, dried bacteria or culture product of *Pediococcus pentosaceus* EROM101, or mutant or variant thereof as an effective ingredient. In addition, excipients or carriers can be added therein. The said 'culture product' comprises the culture solution itself cultured on a liquid medium, the solution left after removing strain by filtering or centrifuging the culture solution (supernatant after centrifuging), and cell lysate resulted from the ultrasonification or lysozyme treatment of the culture solution. The amount of *Pediococcus pentosaceus* EROM101, or mutant or variant thereof in the composition varies depending on the use and formulation form of the composition.

The composition of the invention for immune enhancement, anticancer, antimicrobial, intestinal function-controlling agent or live bacterial agent can be prepared and administered in many formulation forms and by various methods. For example, the *Pediococcus pentosaceus* EROM101, or mutant or variant thereof of the invention can be produced and administered in the form of tablet, troche, capsule, elixir, syrup, powder, suspension or granule, by mixing with carriers and flavoring agents which are used conventionally in the art of pharmaceutics. As such a carrier, binder, lubricator, disintegrating agent, excipient, solubilizer, dispersing agent, stabilizer, suspending agent and the like can be used. The administering route includes oral administration, parenteral administration or plastering, and oral administration is more preferred. The dosage can be determined based on the absorptivity of active ingredients, inactivity rate, excretion speed, age, sex and condition of a patient. And the feed composition of the present invention can be produced in the form of fermented feed, formula feed, pellet feed and silage. The fermented feed can be prepared by adding lactic acid bacteria of the present invention, other microorganisms and enzymes, and fermenting organic substances thereby. Also, the formula feed can be prepared by mixing the *Pediococcus pentosaceus* EROM101, or mutant or variant thereof of the present invention with general feed. The pellet feed can be prepared by formulating the above fermented feed or formula feed with a pelletizing machine. Silage can be prepared by fermenting greenchop feed with the *Pediococcus pentosaceus* EROM101, or mutant or variant thereof of the invention.

Also, the *Pediococcus pentosaceus* EROM101, or mutant or variant thereof of the invention can be used as a food additive for baby food, Kimchi, beverage and the like. Besides, the *Pediococcus pentosaceus* EROM101, or mutant or variant thereof can be used as seed bacteria for preparing fermented products. The fermented products include fermented meat products such as ham and sausage, fermented raw products, Kimchi and the like. The fermented products using the *Pediococcus pentosaceus* EROM101, or mutant or variant thereof of the invention can be prepared by the conventional method well known in the art. For example, in order to prepare fermented raw products, powders of cereals such as brown rice and Job's tears were treated with the lactic acid bacteria of the present invention or 2–3 strains of lactic acid bacteria mixture including the same, leading to the fermentation at a required temperature, and then, various agricultural products such as glutinous rice and sorghum can be added properly to make nutritional balance and good taste.

*Pediococcus pentosaceus* EROM101, or mutant or variant thereof can be mass-produced by the conventional method for culturing a *Pediococcus* genus microorganism. As a culture medium, a medium consisting of carbon source, nitrogen source, vitamin and mineral is available, and for example, MRS (Man-Rogosa-Sharp) medium or milk-added medium can be used. The culture conditions of a microorganism follow the conventional lactic acid bacteria culture conditions, i.e., the microorganism can be cultured at 30 to 45° for 10 to 40 hours. Culturing at 37° for 18 hours is preferred. Centrifugation or filtration can be performed to recover only concentrated bacteria with removing culture medium from the culture solution, and this step can be performed if the skilled in the art deems it necessary. The concentrated bacteria can be frozen or lyophilized not to lose their activities by the conventional method.

The 'effective amount' in this invention refers to enough amount to enhance immunity, or treat cancer or microbial infection in a subject. The term 'subject' as used herein refers to all mammals, and in particular humans. Such subjects are also referred to herein as patients in need of treatment.

The *Pediococcus pentosaceus* EROM101 of the present invention stimulates macrophage proliferation and enhances cellular immunity, humoral immunity and gut immunity (see FIG. 3–FIG. 5 and FIG. 7–FIG. 9). Thus, the present invention provides a method for enhancing immunity in a subject, comprising administering an effective amount of a biologically pure culture of *Pediococcus pentosaceus* EROM101, or mutant or variant thereof into a subject. The preferable administration forms and methods of *Pediococcus pentosaceus* EROM101, or mutant or variant thereof are as explained above.

Figure 10:
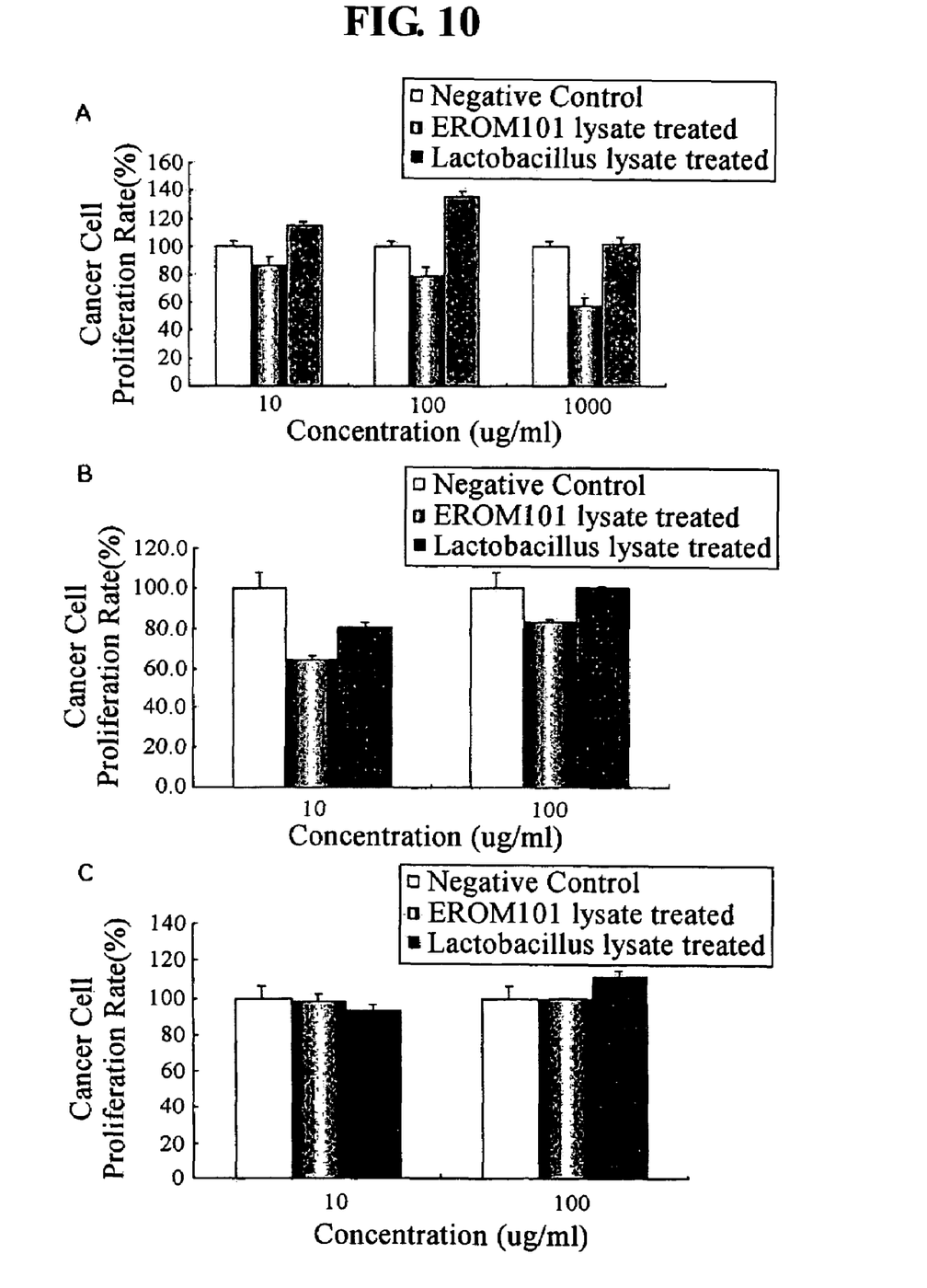
FIG. 10 is a set of graphs showing the anticancer activity of *Pediococcus pentosaceus* of the present invention to stomach cancer cell line (AGS; A), lung cancer cell line (A549; B) and blood cancer cell line (HL60; C). The anticancer activity was obtained by measuring the proliferation rate (%) of cancer cells. The proliferation rate was represented by the percentage to a negative control.
Figure 11:
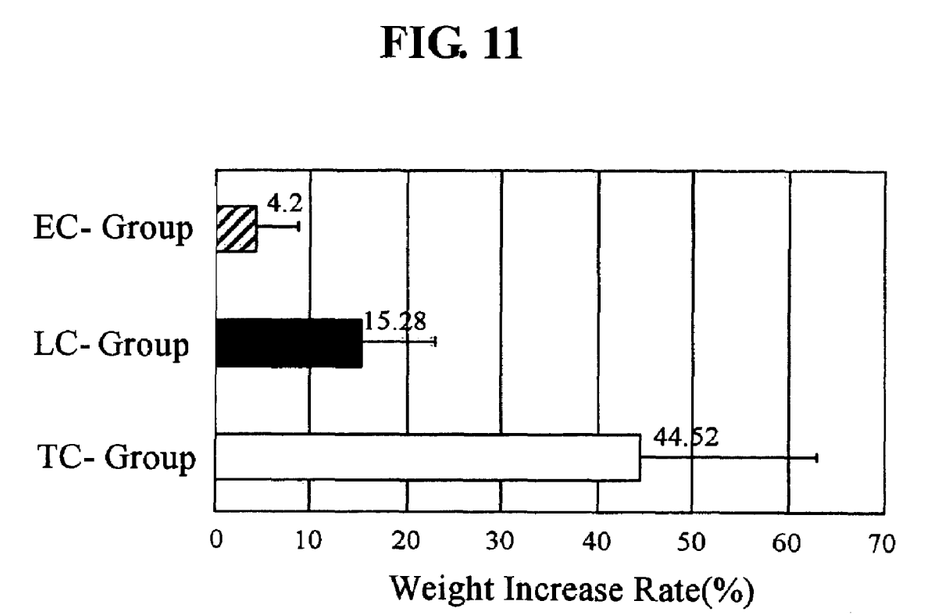
FIG. 11 is a graph showing the weight increase rates of mice, in which ascites cancer was induced, after cell lysate of *Pediococcus pentosaceus* EROM101 of the present invention was administered. The weight increase rates were calculated in terms of the weight increase rates of normal mice without being injected with ascites cancer cells.

The *Pediococcus pentosaceus* EROM101 of the present invention significantly inhibits the cancer cell proliferation (see FIG. 10 and FIG. 11). Thus, the present invention also provides a method for treating cancer in a subject, comprising administering an effective amount of a biologically pure culture of *Pediococcus pentosaceus* EROM101, or mutant or variant thereof into a subject. The above cancers are not limited to, but may include breast cancer, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, vulval cancer, vaginal carcinoma, Hodgkin's disease, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, primary CNS lymphoma, bone marrow tumor, brain stem nerve gliomas, pituitary adenoma, or a combination thereof. Preferably, the cancer might be stomach cancer, lung cancer, blood cancer or ascites cancer. The preferable administration forms and methods of *Pediococcus pentosaceus* EROM101, or mutant or variant thereof are as explained above.

The microorganism *Pediococcus pentosaceus* EROM101 of the present invention has a broad spectrum of activities in vitro with respect to Gram-positive and Gram negative microorganism (see Table 3–5). Therefore, the present invention provides a method for treating microbial infection in a subject, comprising administering an effective amount of a biologically pure culture of *Pediococcus pentosaceus* EROM101, or mutant or variant thereof into a subject. The preferable administration forms and methods of *Pediococcus pentosaceus* EROM101, or mutant or variant thereof are as explained above.

The present invention also provides a method for controlling microbial growth, comprising contacting *Pediococcus pentosaceus* EROM101, or mutant or variant thereof with other microorganisms. The microorganism comprises both Gram-positive bacteria such as *Bacillus cereus, Staphylococcus aureus, Listeria monocytogenes* and Gram-negative bacteria such as *E. coli, Salmonella typhimurium, Vibrio parahaemolyticus, Yersinia enterocolitica*, but is not limited thereto.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Figure 1:
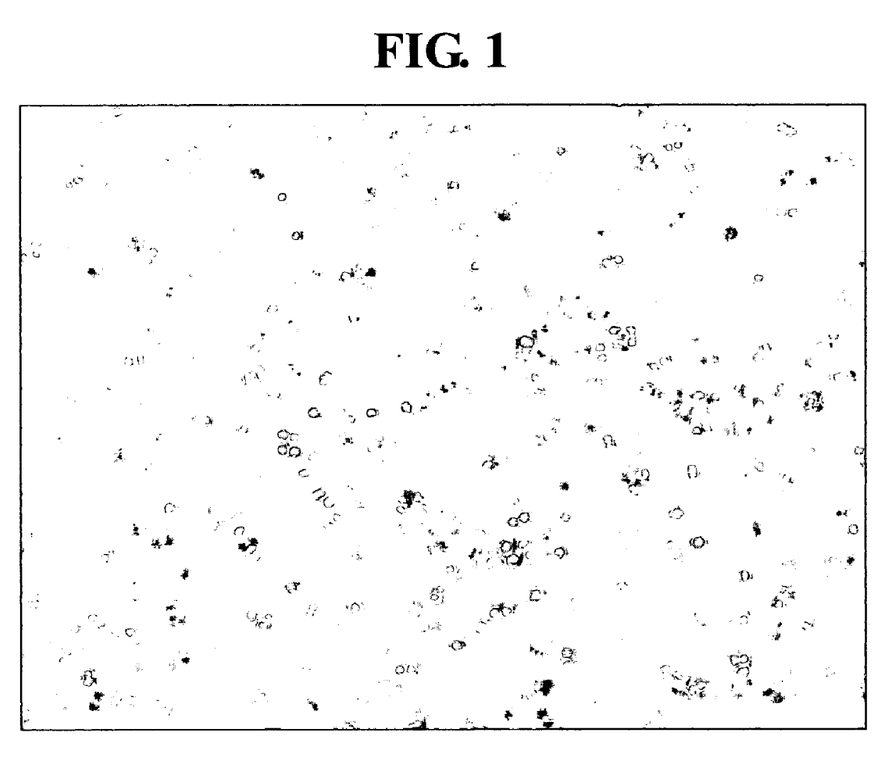
FIG. 1 is a microphotograph showing the *Pediococcus pentosaceus* EROM101 of the present invention.

Separation and Identification of the *Pediococcus* Genus Microorganism of the Present Invention 1 g of human excrements was suspended in 100 Ml of saline, then a required amount was taken therefrom and distributed on LBS agar medium (sodium acetate 25 g/L, glucose 20 g/L, pancreatic digest casein 10 g/L, $KH_2PO_4$ 6.0 g/L, yeast extract 5 g/L, ammonium citrate 2 g/L, polysorbic acid 80 1 g/L, $MgSO_4$ 0.575 g/L, $FeSO_4$ 0.034 g/L, $MnSO_4$ 0.12 g/L, acetic acid 1.32 mL/L, agar 15 g/L, pH 5.5) to separate a single colony. Each colony was inoculated on MRS medium (peptone 10 g/L, yeast extract 5 g/L, beef extract 10 g/L, glucose 20 g/L, polysorbic acid 1 g/L, ammonium citrate 2 g/L, sodium acetate 5 g/L, $MgSO_4$ 0.1 g/L, $MnSO_4$ 0.05 g/L, $Na_2HPO_4$ 2 g/L), and then cultured at 37° for 24 hours. Bacteria were recovered from the culture solution by centrifugation, which were then crushed by ultrasonicator to prepare samples for this experiment. The samples were cultured along with macrophages separated from the abdominal cavity of a Balb/c mouse for 12 hours to select the strain showing the highest macrophage proliferation rate. The macrophage proliferation was investigated by measuring the amount of dye accumulated in the survived cells by taking advantage of neutral red assay. The selected strain was identified using API 50 CHL kit (BioMereux Co., France). The strain was suspended in API CHL medium and distributed on a strip for further culture. The result was interpreted by investigating the change in color of fermented carbohydrates by pH resulting from the generation of acid. All the results were analyzed using API LAB plus database V 5.0, a microorganism identification program. As a result, the selected strain showed 99.9% identity with *Pediococcus pentosaceus*. Thus, the present inventors named the strain '*Pediococcus pentosaceus* EROM101' and deposited it at Korean Culture Center of Microorganism on Oct. 10, 2003 (Accession No: KCCM-10517). FIG. 1 is a microphotograph showing the *Pediococcus pentosaceus* EROM101 of the present invention (referred 'EROM101' hereinafter). The biochemical characteristics of the strain are as follows and the sugar utilization was listed in Table 1.

<Characteristics of the Strain>

1. Growth temperature: Grow well at 30–45°, cannot grow at 15° (optimum growth temperature: 37°)
2. Growth pH: 6–7 (optimum growth pH: 6.5)
3. Mobility: None
4. Gram staining: Positive
5. α-glucosidase activity: Positive, β-galactosidase activity: Negative
6. Oxygen requirement: Facultative anaerobic

TABLE 1

Sugar utilization of *Pediococcus pentosaceus* EROM101 of the invention

| Sugar | Reaction | Sugar | Reaction |
|---|---|---|---|
| Glycerol | − | Salicine | + |
| Erythritol | − | Cellobiose | + |
| D-arabinose | − | Maltose | + |
| L-arabinose | + | Lactose | + |
| Ribose | + | Melibiose | + |
| D-xylose | + | Saccharose | + |
| L-xylose | − | Trehalose | + |
| Adonitol | − | Inuline | − |
| βmethyl-xyloside | − | Melezitose | − |
| Galactose | + | D-Raffinose | + |
| D-glucose | + | Amidon | − |
| D-fructose | + | Glycogene | − |
| D-mannose | + | Xylitol | − |
| L-Sorbose | − | β Gentiobiose | + |
| Rhamnose | − | D-Turanose | − |
| Dulcitol | − | D-Lyxose | − |
| Inositol | − | D-Tagatose | + |
| Mannitol | − | D-Fucose | − |
| Sorbitol | − | L-Fucose | − |
| α-methyl-D-mannoside | − | D-Arabitol | − |
| α-methyl-D-glucoside | − | L-Arabitol | − |
| N-acetylglucosamine | + | Gluconate | − |
| Amygdaline | + | 2-keto-gluconate | − |
| Arbutine | + | 5-keto-gluconate | − |
| Esculine | + | | |

Example 2

Investigation of the Immune Enhancement Activity of EROM101: In Vitro Test

Figure 2:
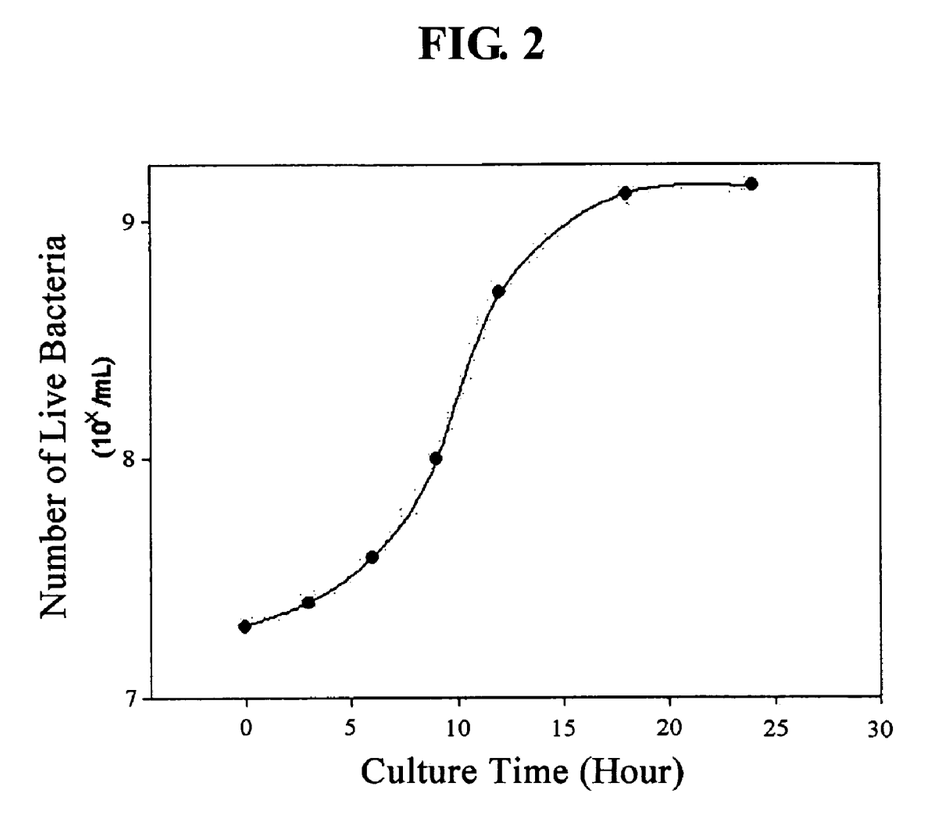
FIG. 2 is a graph showing the number of live bacteria according to the culture time of the *Pediococcus pentosaceus* EROM101 of the present invention.

<2-1> Investigation of Proliferation Rate and Activity of Macrophage a) Measuring Proliferation Rate of Macrophage In order to investigate the immune enhancement activity of EROM101 separated in the Example 1, the viable cells were measured according to culturing time. The pre-cultured strain was inoculated on MRS medium to 2% of the final density, which was further cultured at 37°. During the culturing, viable cells were measured according to culturing time. As a result, as shown in FIG. 2, the maximum viable cells were observed when they ha been cultured for 18 hours.

Figure 3:
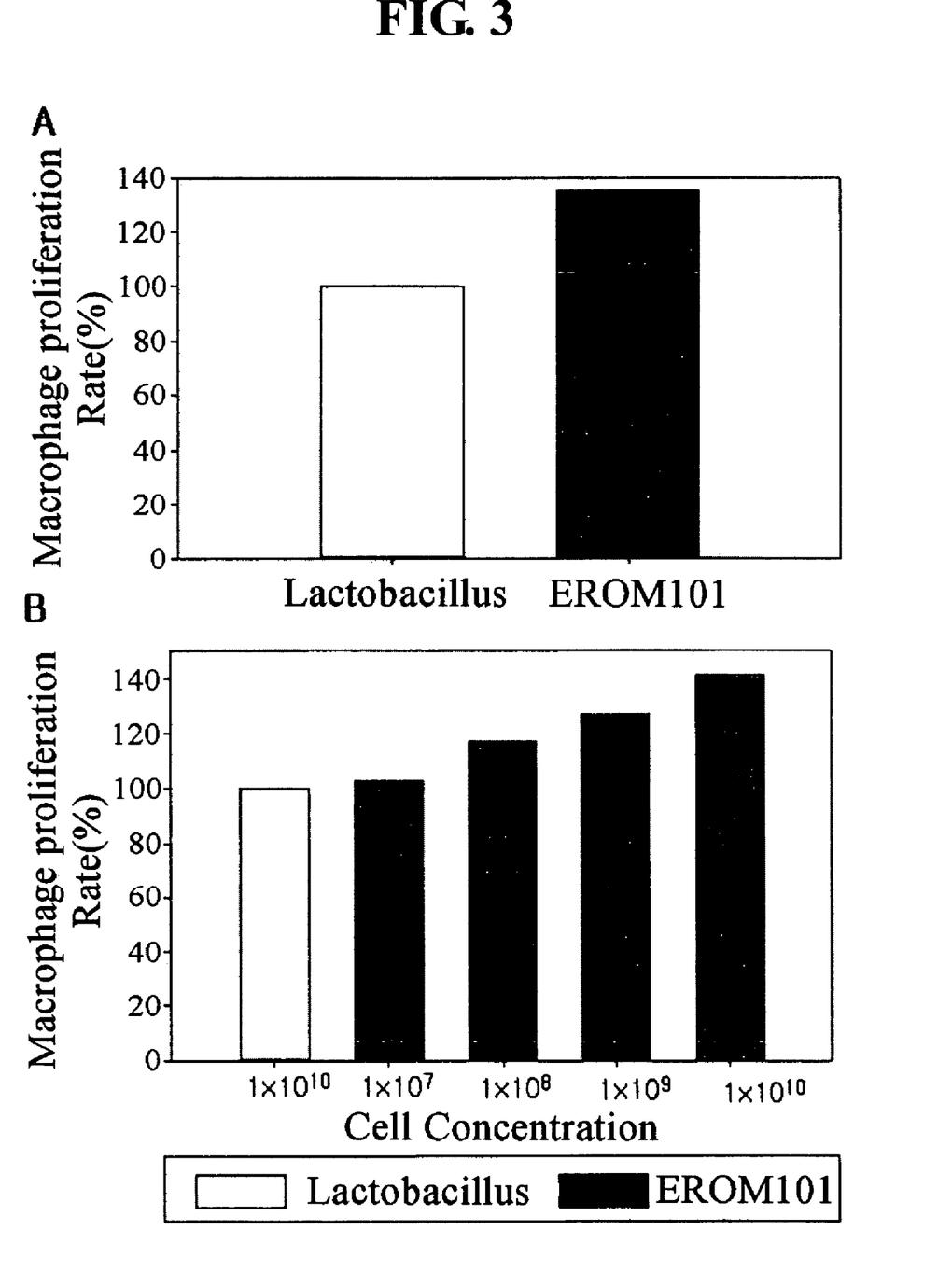
FIG. 3 is a set of graphs showing the proliferation rate (%) of macrophages induced by the *Pediococcus pentosaceus* EROM101 of the present invention. The proliferation rate was represented by the percentage to the proliferation rate of macrophages induced by *Lactobacillus acidophilus*, a test strain.

In order to confirm the immune enhancement activity of EROM101 of the present invention, EROM101 pre-cultured for 18 hours was further cultured for 24 hours with macrophages originated from the abdominal cavity of mice as seen in Example 1. At this time, *Lactobacillus acidophilus* (ATCC 43121), a test strain was used as a control. Macrophage proliferation rate was investigated by the same method used in Example 1, and was represented by the percentage to that of a control group. As a result, as shown in FIG. 3A, macrophage proliferation by EROM101 of the invention was much higher than that by *Lactobacillus acidophilus*. Also, in order to investigate the macrophage proliferation rate by measuring viable cells, EROM101 pre-cultured for 18 hours was diluted to each concentration and macrophages originated from mice were added to each concentration for co-culture. As a result, as shown in FIG. 3B, macrophage proliferation was increased depending on cell concentration. From the result, it was confirmed that EROM101 of the present invention stimulates macrophage proliferation in high level.

b) Investigating Activity of Macrophage

1 Ml of sterilized thioglycollate (Sigma-Aldrich, USA) was injected into the abdominal cavity of a 5 week old Balb/c mouse (Daehan Biolink, Korea), followed by the activation for 72 hours. Then, its cervical vertebra was dislocated. 5 Ml of RPMI 1640 medium (Gibco, N.Y., USA) was injected into the abdominal cavity of the mouse for washing. After the washing, the medium was recovered. The procedure was repeated 2–3 times. The recovered solution was centrifuged at 4° with 1,500 rpm for 10 minutes, which was suspended in a medium to the cell number of $1 \times 10^6$ cells/Ml. The solution was distributed into a 96-well plate by 100 µl per each well and the final cell density was adjusted to $1 \times 10^5$ cells/Ml. The plate was cultured in a 5% $CO_2$ incubator at 37° for 2 hours. It was confirmed whether macrophages were fixed on the plate to form a monolayer. The culture solution was removed from the plate, then live EROM101 and cell lysate thereof were added to RPMI 1640 medium (+10% FBS) by concentrations (1 µg, 10 µg, 100 µg and 1 mg). The medium was distributed by 200 µl per each well. The said live bacteria were prepared by filtrating the cell culture solution ($1 \times 10^9$ cells therein) through 0.2 µm filter. The preparation of the said lysate was as follows; the cell culture solution was centrifuged with 6,000 rpm for 15 minutes, and the supernatant was removed and washed with PBS twice. Lysozyme from hen egg white (Fluka Co. Switzerland) was treated thereto by the concentration of 0.1 g/10 ml, which was left in a 37° shaking incubator for 1 hour and filtered by 0.2 µm filter. In the meantime, RPMI 1640 medium (+10% FBS) containing 20 µl of LPS (lipopolysaccharide; B-cell inducing substance extracted from *E. coli*) was distributed for a positive control, and the medium was distributed for a negative control. Macrophages were activated by means of culturing in a 5% $CO_2$ incubator for 24 hours. Macrophage activity was investigated by measuring the activity of enzyme (lysosomal enzyme) that was secreted during the macrophage activation. After completing the culture, supernatant was removed. 25 µl of 0.1% triton-X-100 was added, followed by a reaction in an incubator for 20 seconds. 150 µl of 100 mM ρ-nitrophenyl phosphate and 50 µl of 0.1 M citrate buffer solution (pH 6.0) were added thereto, followed by a reaction in a 37° 5% $CO_2$ incubator for 45 minutes. The reaction was stopped by adding 50 µl of 0.2 M borate buffer solution (pH 9.6). $OD_{405}$ was measured with ELSIA reader (TECAN GENios, Austria).

Figure 4:
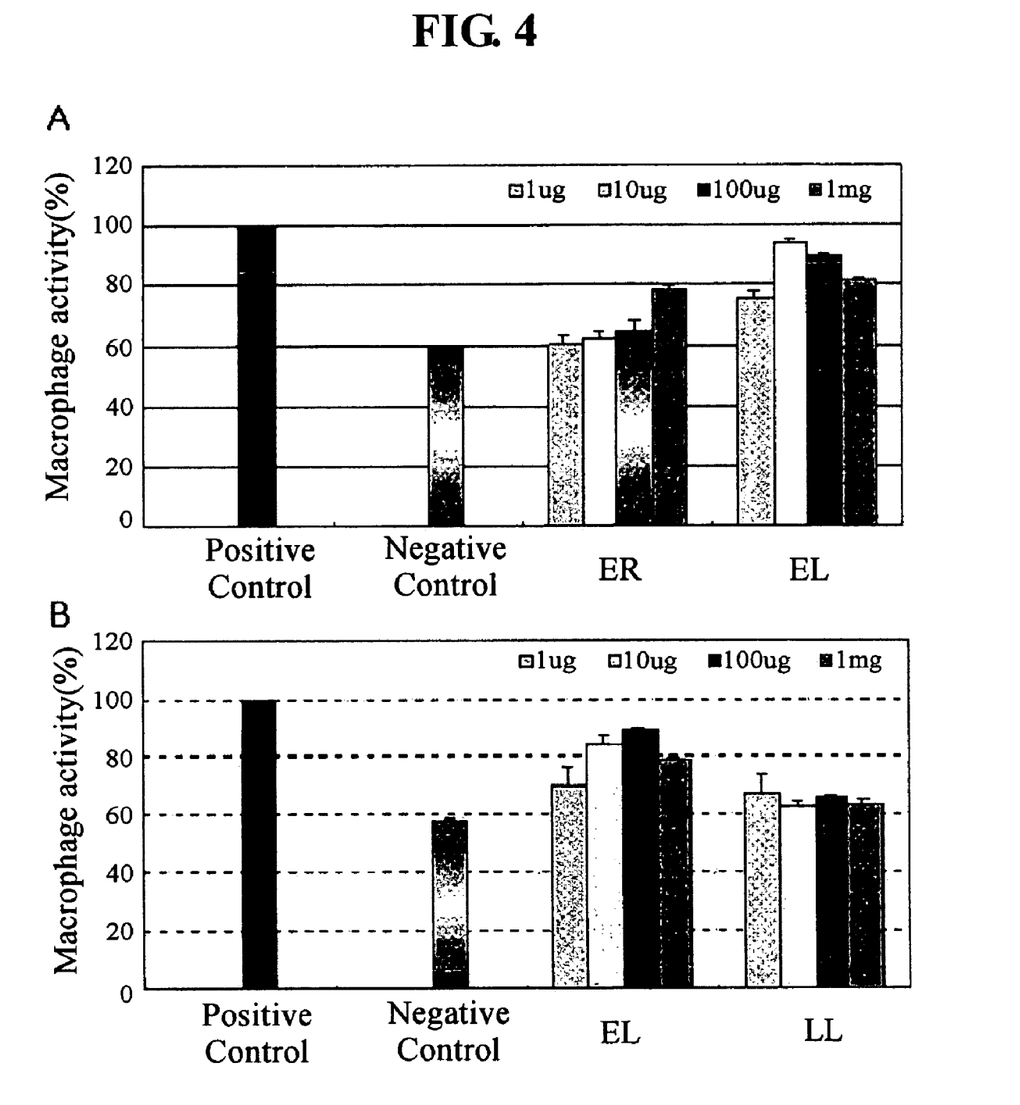
FIG. 4 is a set of graphs showing the macrophage activity (%) induced by the *Pediococcus pentosaceus* EROM101 of the present invention. The activity was represented by the percentage to a positive control.

As a result, as shown in FIG. 4A, the lysate of EROM101 of the present invention showed higher macrophage activity than live EROM101. The maximum activity of the lysate was 93.84%, which was very high compared to that of a positive control (LPS-treated group)(100%).

c) Comparison of the Macrophage Activity Between EROM101 and Test Strain

The macrophage activity of EROM101 of the present invention was compared with that of *Lactobacillus acidophilus* (ATCC 43121), a test strain. The investigation procedure was the same as used in the above b). As a result, as shown in FIG. 4B, EROM101 of the present invention showed much higher macrophage activity than *Lactobacillus acidophilus*.

<2-2> Investigation of the Spleen Cell Activity

The spleen of a 5-week-old Balb/c mouse was taken out and spleen cells were separated therefrom using a mesh. Centrifugation was performed at 4° with 1,700 rpm for 5 minutes and the supernatant was removed. After washing with RPMI 1640 medium twice, 3 Ml of lysis buffer (155 mM $NH_4Cl$, 10 mM $KHCO_3$, 0.1 mM EDTA) was added in order to eliminate red blood cells included in the spleen cell solution. After it had been put in a 37° water bath for 5 minutes, centrifugation was performed again at 4° with 1,700 rpm for 5 minutes. Supernatant was removed, followed by washing with RPMI 1640 medium twice. The final concentration of the cell solution was adjusted to $5 \times 10^6$ cells/Ml and then the solution was distributed to each well of a 96-well plate by 200 μl. The lysate of EROM101 of the present invention and the lysate of *Lactobacillus acidophilus* (ATCC 43121) were grouped by concentrations for further treatment. The said lysates were prepared by the same method as used in Example <2-1> b). 10 μg/μl of LPS was treated to a positive control and the sterilized water was treated to a negative control. The spleen cell activity was investigated by measuring the proliferation rate of the spleen cell using MTS assay. After it had been cultured in 5% $CO_2$ incubator at 37° for 72 hours, 20 μg/Ml of MTS (CellTiter 96 Aqueous One Solution Cell Proliferation Assay. Promega, Cat No: G3580) was treated thereto, followed by a reaction for 1–3 hours. $OD_{492}$ was measured with ELISA reader (TECAN GENios, Austria).

Figure 5:
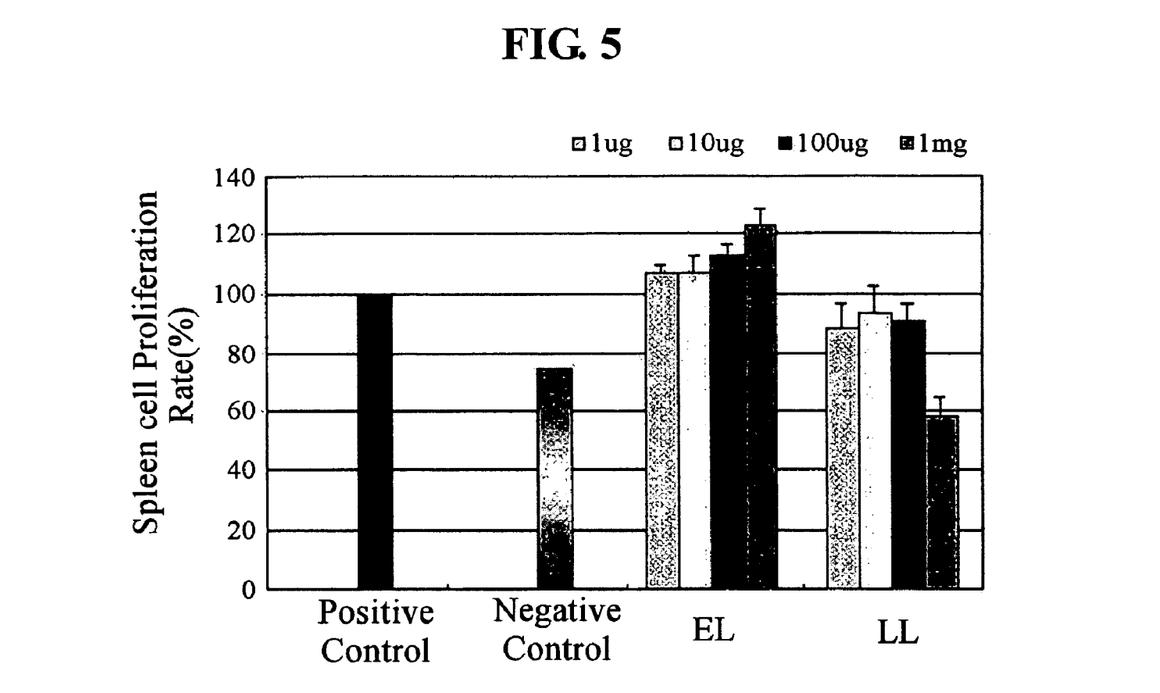
FIG. 5 is a graph showing the proliferation rate (%) of spleen cells induced by the *Pediococcus pentosaceus* EROM101 of the present invention. The proliferation rate was represented by the percentage to a positive control.

As a result, as shown in FIG. 5, EROM101 of the present invention showed much higher spleen cell activity than *Lactobacillus acidophilus*, a test strain. The maximum activity was 123.13%, which was very high compared to that of a positive control (100%).

Example 3

Investigation of Immune Enhancement Activity of EROM101: In Vivo Test

<3-1> Sample Ingestion 3 week old Balb/c female mice (Daehan Biolink, Korea) were classified, by 6 mice per each group, into 5 groups; 1) control group (sterilized water administered group), 2) live EROM101 orally-administered group (ER), 3) EROM101 lysate orally-administered group (EL), 4) live *Lactobacillus* orally-administered group (LR), and 5) *Lactobacillus* lysate orally-administered group (LL), to which 200 μl of each sample were orally administered once a day for 4 weeks. Except filtering process, the said live bacteria and lysate were prepared by the same methods as used in Example <2-1> b). In the experiments for investigating the activities of macrophages, spleen cells and gut immunity, LPS, a B-cell inducing material, and ConA (concanvalinA), a T-cell inducing material, were used by 10 μg/Ml, respectively, for a positive control. The mice of each group were raised under the fixed condition in which temperature was set at 32±2°, humidity was set to ±20%, and the light exposure for 12 hours (from AM 07:00 to PM 07:00). Solid feed for a mouse and tap water were given to the mice freely.

Figure 6:
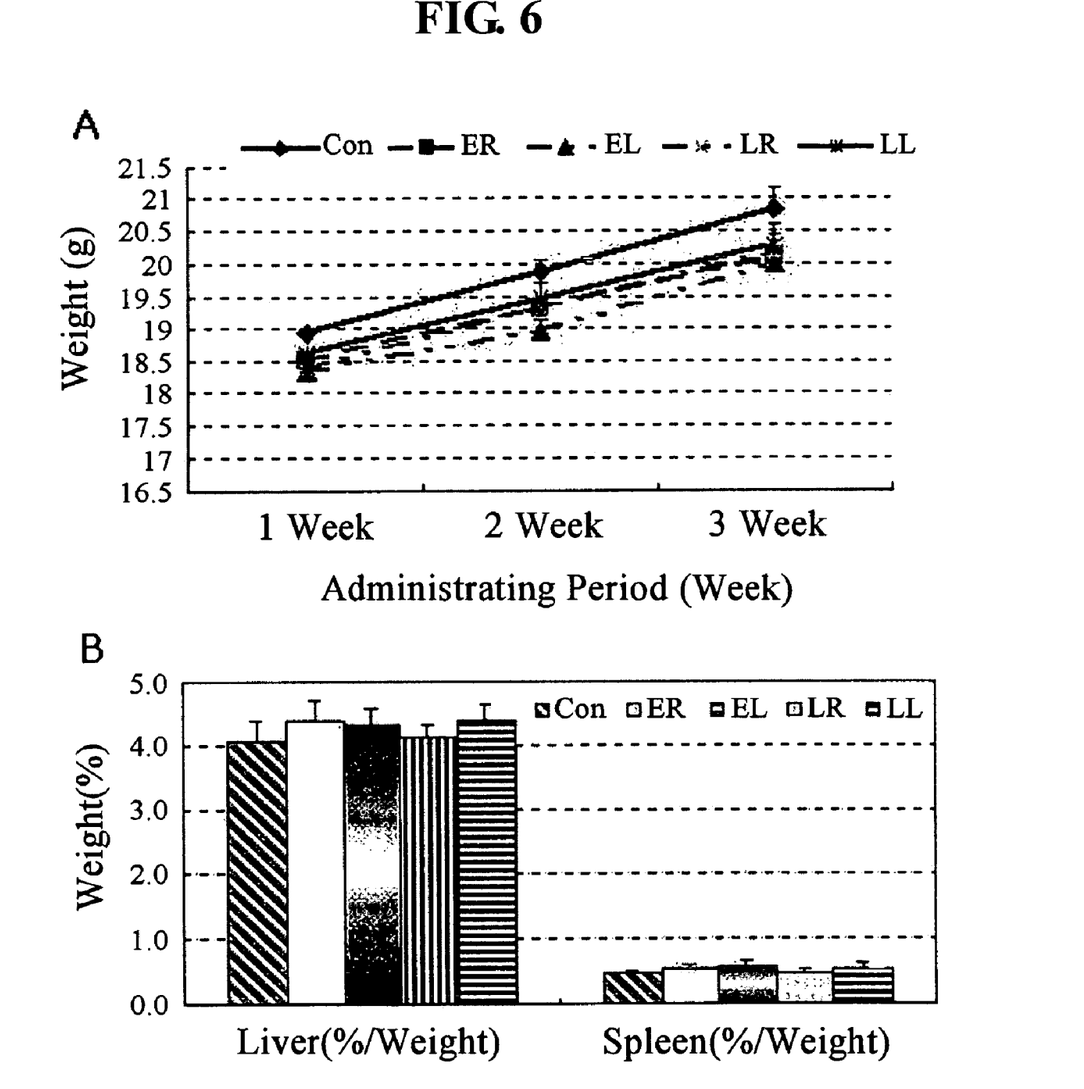
FIG. 6 is a set of graphs showing the weight changes (A) of mice while the *Pediococcus pentosaceus* EROM101 of the present invention was administered orally, and tissue weight (B) measured after 4 weeks with oral administration.

<3-2> Measuring the Change in Total Weight and the Weight of the Internal Organs Weight changes were observed to investigate the growth of the mice of each group. As a result, as shown in FIG. 6A, there were no significant changes in both experimental groups and control groups. In order to investigate if the internal organs of each mouse were normal, the abdominal cavities of mice were opened 4 weeks after the oral administration and the internal organs (spleen and liver) were separated to measure their weights. As a result, as shown in FIG. 6B, all the groups showed similar aspects.

<3-3> Measuring Biochemical and Hematological Indexes in Blood 4 weeks after the oral administration, blood was taken from orbit, and serum was separated from each mouse. Biochemical indexes in blood—liver functional indexes (GOT and GPT) and kidney functional indexes (BUN and creatine)—were measured by a biochemical analyzer (Cobas Mira plus), and hematological indexes (red blood cell, platelet and blood figment) were also measured by a blood corpuscle analyzer (Medonic Ca 620, Boule, Sweden). As a result, as shown in below Table 2, the biochemical and hematological indexes of the mice from every group were all normal.

TABLE 2

Biochemical and hematological indexes

| | Index measured | Normal range | Group | Measured value (Mean ± SD) |
|---|---|---|---|---|
| Biochemical Index | GOT | Under 247 U/L | Control | 85.9 ± 8.99 |
| | | | [a]ER | 104.46 ± 11.22 |
| | | | [b]EL | 117.72 ± 24.47 |
| | | | [c]LR | 110.27 ± 7.87 |
| | | | [d]LL | 130.18 ± 7.87 |
| | GPT | Under 132 U/L | Control | 28.67 ± 1.96 |
| | | | ER | 33.98 ± 2.11 |
| | | | EL | 36.86 ± 5.85 |
| | | | LR | 30.72 ± 4.17 |
| | | | LL | 37.56 ± 5.02 |
| | BUN | Under 29 U/L | Control | 28.59 ± 3.97 |
| | | | ER | 26.12 ± 4.61 |
| | | | EL | 26.26 ± 4.47 |
| | | | LR | 27.63 ± 5.49 |
| | | | LL | 26.61 ± 3.41 |
| | Creatine | Under 0.9 U/L | Control | 0.65 ± 0.14 |
| | | | ER | 0.84 ± 0.14 |
| | | | EL | 0.73 ± 0.16 |
| | | | LR | 0.66 ± 0.09 |
| | | | LL | 0.77 ± 0.08 |
| Hematological Index | RBC | 6–12 | Control | 9.42 ± 0.54 |
| | | | ER | 8.69 ± 0.77 |
| | | | EL | 10.66 ± 0.27 |
| | | | LR | 9.39 ± 0.49 |
| | | | LL | 8.93 ± 0.54 |
| | PLT | 190–1000 | Control | 431.75 ± 192.12 |
| | | | ER | 423.83 ± 182.84 |
| | | | EL | 577.5 ± 66.11 |
| | | | LR | 673.75 ± 86.44 |
| | | | LL | 437.75 ± 75.61 |
| | HGB | 12–17 | Control | 14.25 ± 0.66 |
| | | | ER | 13.8 ± 2.9 |
| | | | EL | 18.4 ± 0.81 |
| | | | LR | 16.9 ± 1.62 |
| | | | LL | 13.82 ± 0.65 |

[a]ER: Group administered orally with live ERM101 of the present invention
[b]EL: Group administered orally with cell lysate of EROM101 of the present invention
[c]LR: Group administered orally with live *Lactobacillus acidophilus*
[d]LL: Group administered orally with cell lysate of *Lactobacillus acidophilus*

<3-4> Investigation of Macrophage Activity

Figure 7:
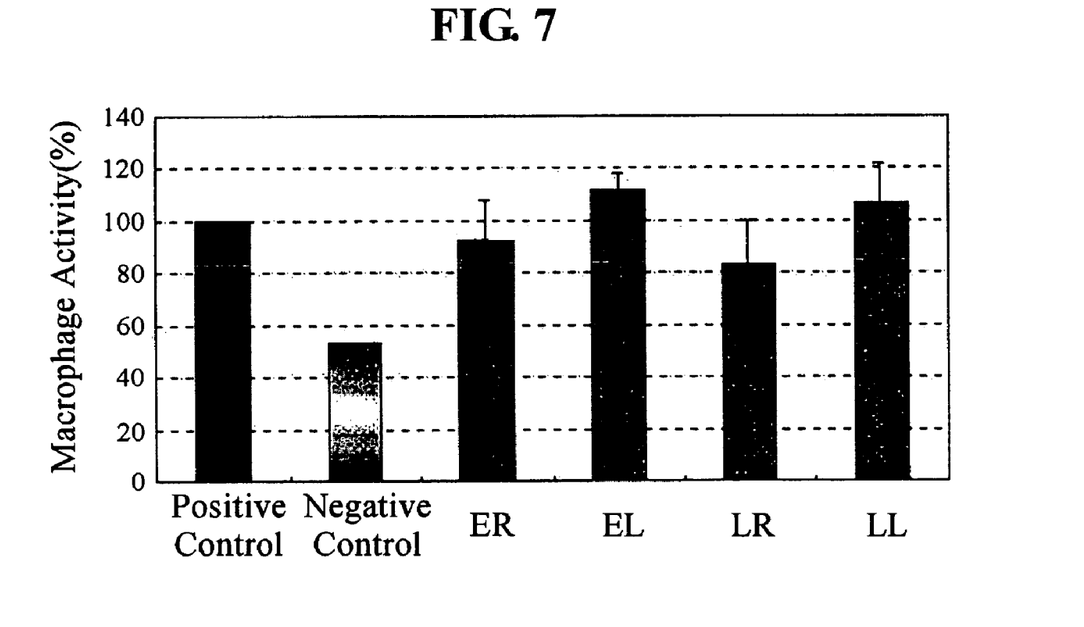
FIG. 7 is a graph showing the macrophage activity of mice administered orally with the *Pediococcus pentosaceus* EROM101 of the present invention. The activity was represented by the ratio to a positive control.

Macrophages were separated from each mouse of every group. The macrophage activity was investigated by measuring the activity of an enzyme secreted during the macrophage activation using the same method as used in the above Example <2-1> b). As a result, as shown in FIG. 7, the highest activity was seen in EROM101 lysate orally-administered group (EL) and *Lactobacillus* lysate orally-administered group (LL), live EROM101 orally-administered group (ER) and live *Lactobacillus* orally-administered group (LR) follows in that order. In addition, the EROM101 lysate orally-administered group showed higher activity than the positive control group.

<3-5> Investigation of Spleen Cell Activity

Figure 8:
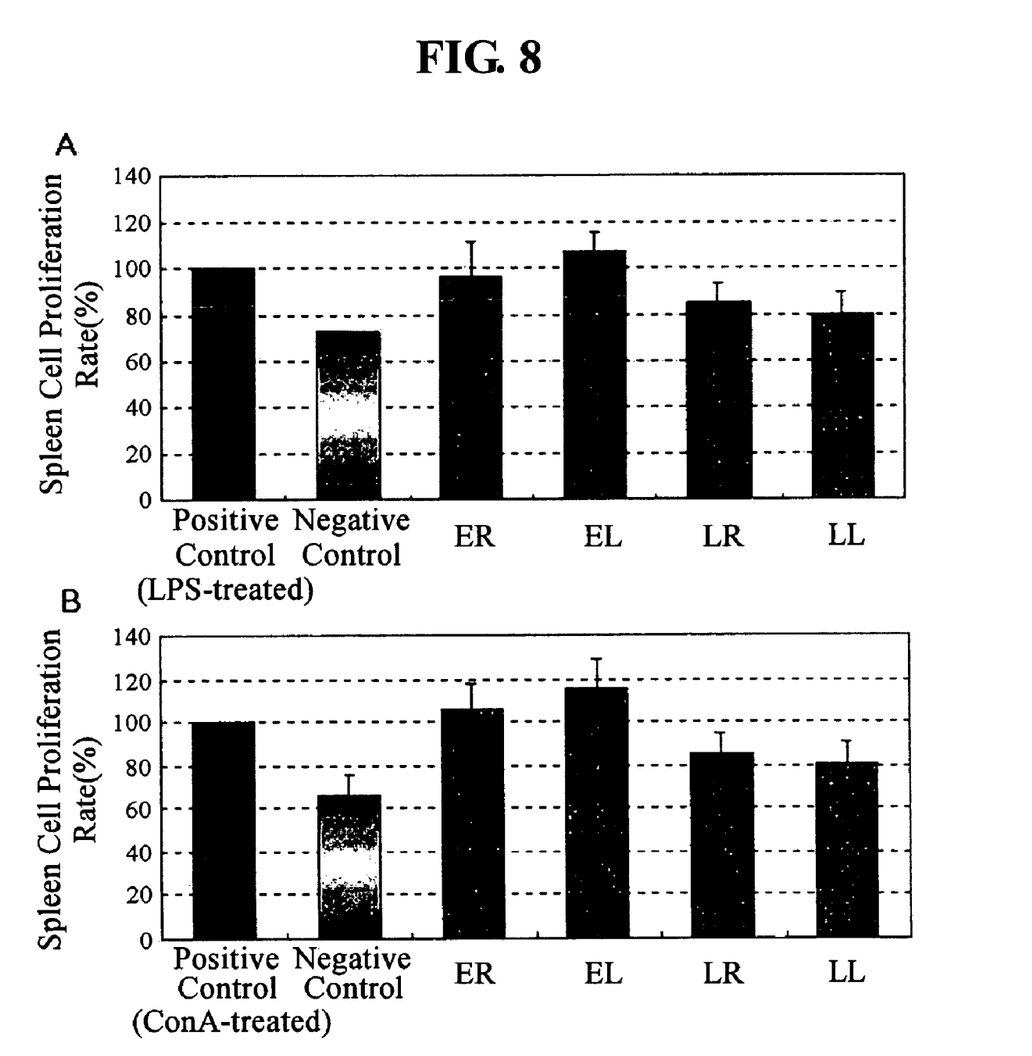
FIG. 8 is a set of graphs showing the proliferation rate (%) of spleen cells of mice administered with the *Pediococcus pentosaceus* EROM101 of the present invention. The proliferation rate was represented by the percentage to a positive control.

Spleen cells were separated from each mouse of every group by using same method as Example <2-2> to investigate the spleen cell activity by using MTS assay. As a result, as shown in FIG. 8, the highest activity was seen in EROM101 lysate orally-administered group (EL) and live EROM101 orally-administered group (ER), *Lactobacillus* lysate orally-administered group (LL) and live *Lactobacillus* orally-administered group (LR) follows in that order. Particularly, EROM101 lysate orally-administered group (EL) showed higher activity than the positive controls, LPS treated group and ConA treated group.

<3-6> Investigation of the Activity of Gut Immunity

In order to investigate the activity of gut immunity, the amount of IgA secreted in peyer's patch was measured. First, all mice were sacrificed by dislocation of cervical vertebrae. Then, the abdominal cavities of the mice were opened to take out small intestines. Peyer's patch was separated to extract target cells using a mesh. The obtained cells were suspended in RPMI 1640 medium (+10% FBS) by the concentration of $1 \times 10^6$ cells/ml. The suspension was distributed by 1 Ml to each well of a 24-well plate. 10 μg/Ml of LPS was additionally treated to some wells (positive control). Peyer's patch was activated by culturing the plate in 5% $CO_2$ incubator at 37° for 5 days. After finishing the culture, supernatant was taken to measure the total antibody content of IgA. For that purpose, anti-mouse IgA antibody (Phamingen, USA) was fixed on a 96-well plate, to which Block ace (PBS containing 10% FBS) was treated, resulting in the inhibition of unspecific binding of antibody. Then, the sample containing IgA was mixed. The reaction with peroxidase-conjugated anti-mouse IgA antibody (Phamingen, USA) was followed. $OD_{450}$ was measured with ELISA reader (TECAN GENios, Austria).

Figure 9:
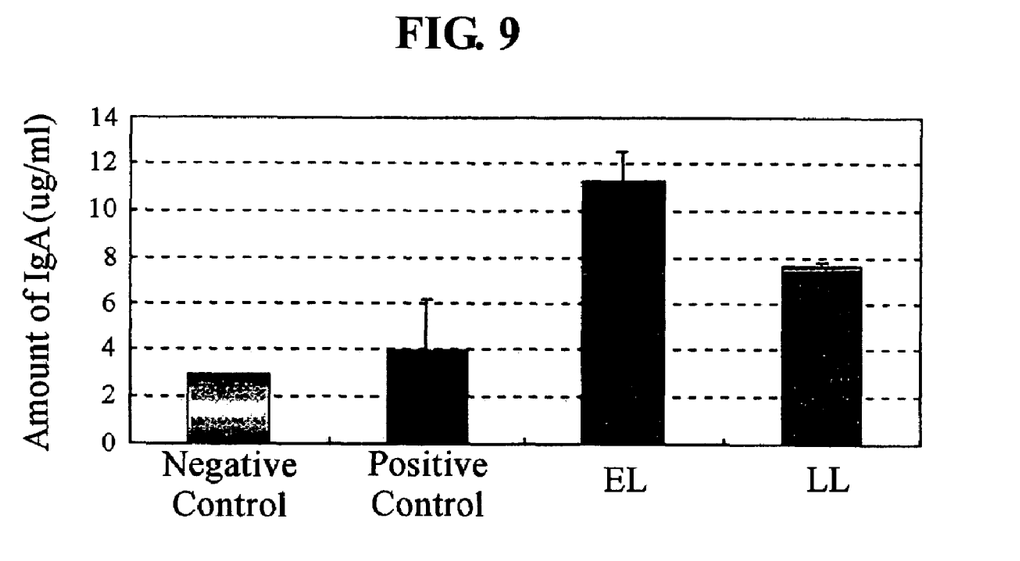
FIG. 9 is a graph showing the amount of IgA secreted from mucosal membrane epithelial cells of the mice administered orally with the *Pediococcus pentosaceus* EROM101 of the present invention.

As a result, as shown in FIG. 9, EROM101 lysate administered group showed the highest IgA generation, which was 2.8 times higher than that of the positive control.

From all the above results, EROM101 of the present invention has been confirmed to have much more excellent immune enhancement activity than *Lactobacillus acidophilus*, a test strain.

Example 4

Investigation of the Anticancer Activity of EROM101

<4-1> In Vitro Test

In order to investigate the anticancer activity of EROM101 of the present invention, the capability of EROM101 to inhibit the cancer cell proliferation in human cancer cell lines was measured. The stomach cancer cell line AGS (adenocarcinoma, stomach, human, KCLB No.21739), the lung cancer cell line A549 (carcinoma, lung, human, KCLB N. 10185), and the blood cancer cell line HL60 (leukemia, blood, human, KCLB No. 10240) were distributed in a 96-well plate by $2.0-2.5 \times 10^4$ cells/Ml per each well. EROM101 lysate and *Lactobacillus acidophilus* (test strain, ATCC 43121) lysate were treated by concentrations, which were, then, cultured for 24 or 72 hours. RPMI 1640 medium containing heat-inactivated FBS, 100 μg/Ml penicillin and 100 μg/Ml streptomycin was used for the culture in 5% $CO_2$ (95% air) incubator at 37°. The said lysate was prepared by the same method as used in the above Example <2-1> b). Serum-free medium was treated to a negative control. After finishing the culture, 20 μl of MTS (Cat. No. G3581, Promega Co., USA) was treated to induce color development. In one hour, $OD_{492}$ was measured with ELISA reader (TECAN GENios, Austria).

As a result, as shown in FIG. 10, EROM101 of the present invention was confirmed to significantly inhibit cancer cell proliferation in stomach, lung, blood cancer cell lines, comparing to *Lactobacillus acidophilus*, a test strain. Particularly, the inhibition effect was at maximum 42.5% in a stomach cancer cell line, 35.5% in a lung cancer cell line, and was high depending on concentration in a stomach cancer cell line. All the results were statistically significant.

<4-2> In Vivo Test 8 week old 40 ICR mice (Daehan Biolink, Korea) were classified into 4 groups and $1 \times 10^6$ sarcoma 180 cell line (KCLB 40066) were injected into the abdominal cavities of the mice in three groups to induce ascites cancer. Two of the above three groups were treated with EROM101 lysate and *Lactobacillus acidophilus* (ATCC 4356) lysate every other day after the sarcoma 180 cell line injection, respectively. The lysates were injected into the abdominal cavities of mice once two day for 14 days. The said lysates were prepared by the same method as used in Example <2-1> b) except filtering. One of the above three groups was injected with saline using the same method as said two groups. The above four groups were as follows; 1) N-group in which cancer cells were not injected, 2) TC-group in which saline was injected in their abdominal cavity after the injection of cancer cells, 3) EC-group in which EROM101 lysate was injected in their abdominal cavity after the injection of cancer cells, and 4) LC-group in which *Lactobacillus acidophilus* lysate was injected in their abdominal cavity after the injection of cancer cells. All the mice of each group were raised under the pathogen-free, standard conditions. For the next two weeks, the weight changes caused by the increase of ascites cancer cells were observed. The increased weight was converted into the increase rate to the weight of N-group mice in which cancer cells were not injected, leading to the determination of anticancer effect by immune enhancement.

As a result, as shown in FIG. 11, the weight increase rate was 44% in TC-group compared to N-group, which seemed to be caused by the growth of ascites cancer cells. And the weight increase rate of LC-group injected with *Lactobacillus acidophilus* was 15%, compared to the rate of TC-group. On the other hand, EC-group injected with EROM101 of the invention showed only 4% weight increase. Therefore, EROM101 of the present invention was confirmed to have an anticancer activity.

Example 5

Investigation of the Antimicrobial Activity of EROM101

<5-1> Investigation of the Antimicrobial Activity to Gram-positive and Gram-negative Bacteria EROM101 of the present invention was cultured in 250 Ml Erlenmeyer flask at 35° for 48 hours. At that time, volume was adjusted to 100 Ml and MRS medium (Difco Lab., USA) was used. As test strains for the investigation of the antimicrobial activity, the strains listed in Table 3 were used. TSA medium (Difco Lab., USA) was used for the culture. The antimicrobial activity of EROM101 of the present invention was investigated by using paper disk method. 5.5 Ml of soft agar (0.75%), on which the test strain was inoculated, was piled up on the TSA medium to prepare a plate for the investigation of the antimicrobial activity. On that plate, paper disk (8 mm in diameter) (Adventec Toyo RoshiKaisha, Ltd., Japan) was placed, onto which the culture broth, supernatant and cell lysate of EROM101 were distributed by 80μl respectively, followed by a further culture at 37° for 18 hours. The supernatant was obtained by centrifuging the culture broth at 4° with 8,000 rpm. In order to obtain the lysate, PBS was added to the pellet generated from the above centrifugation to prepare suspension. And the suspension was treated with sonic Dismenbrator (Model 500 Fisher scientific USA), resulting in lysate. The generation of a growth inhibition ring was identified.

As a result, as shown in Table 3, EROM101 of the present invention was confirmed to inhibit the growth of all test strains. The antimicrobial activity was detected in the culture broth and the supernatant, but not in the lysate.

TABLE 3

Antimicrobial activity of EROM101

| Type | Test Strain | Inhibition | | |
|---|---|---|---|---|
| | | Culture Broth | Supernatat | Lysate |
| Gram-positive | Bacillus cereus, ATCC 14579 | + | + | − |
| | Staphylococcus aureus, KCTC 1621 | + | + | − |
| | Listeria monocytogenes, KFRI 799 | + | + | − |
| Gram-negative | Escherichia coli, ATCC 11775 | + | + | − |
| | Escherichia coli O 157:H7 933 | + | + | − |
| | Salmonella typhimurium, ATCC 12023 | + | + | − |
| | Vibrio parahaemolyticus, KCCM 41664 | + | + | − |
| | Yersinia enterocolitica, KTCC 9610 | + | + | − |

<5-2> Comparison of the Antimicrobial Activity of EROM with Test Strains

The antimicrobial activity of EROM101 of the present invention was compared with those of *Pediococcus pentosaceus* (KCCM 11902) and *Lactobacillus acidophilus* (ATCC 43121). At that time, *Bacillus cereus* (ATCC 14579) and *Listeria monocytogenes* (KFR1799) were used as indicators. For the investigation of the antimicrobial activity, the above two indicator bacteria were smeared on TSA agar plate by $1 \times 10^6$ CFU/Ml using a cotton rod. The growth inhibition ring was confirmed by using the same method as used in the above Example <5-1>. The antimicrobial activity unit was calculated by assuming that 1 AU (Arbitrary Unit) is determined to be 1 $mm^2$ which is the size of the remaining dimensions after subtracting the dimensions of paper disk from the dimensions of the generated growth inhibition ring.

As a result, as shown in Table 4 and Table 5, EROM101 of the present invention showed much higher antimicrobial activity against the two indicators than other test strains.

TABLE 4

Antimicrobial activity of EROM101 to *Bacillus cereus*

| Strain | Antimicrobial activity (AU) |
|---|---|
| EROM101 | 72 |
| *Pediococcus pentosaceus* KCCM 11902 | 44 |
| *Lactobacillus acidophilus* ATCC 43121 | 28 |

TABLE 5

Antimicrobial activity of EROM101 to *Listeria monocytogenes*

| Strain | Antimicrobial activity (AU) |
|---|---|
| EROM101 | 209 |
| *Pediococcus pentosaceus* KCCM 11902 | 126 |
| *Lactobacillus acidophilus* ATCC 43121 | 87 |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A biologically pure culture of a microorganism *Pediococcus pentosaceus* EROM101 having the Accession number KCCM-10517.

* * * * *